United States Patent [19]
Pang et al.

[11] Patent Number: 5,861,313
[45] Date of Patent: Jan. 19, 1999

[54] METHOD OF ISOLATING BILE DUCT PROGENITOR CELLS

[75] Inventors: Kevin K. Pang, Belmont; Monica W. Homa, Marblehead, both of Mass.

[73] Assignee: Ontogeny, Inc., Cambridge, Mass.

[21] Appl. No.: 478,064

[22] Filed: Jun. 7, 1995

[51] Int. Cl.$^6$ .................................................. C12N 5/06
[52] U.S. Cl. .................... 435/347; 435/370; 435/373; 435/384; 435/387; 435/392
[58] Field of Search .................... 435/347, 370, 435/373, 384, 387, 392; 424/93.21

[56] References Cited

U.S. PATENT DOCUMENTS

| | | | |
|---|---|---|---|
| 4,298,002 | 11/1981 | Ronel et al. | 128/260 |
| 5,061,620 | 10/1991 | Tsukamoto et al. | 435/7.21 |
| 5,087,570 | 2/1992 | Weissman et al. | 435/240.1 |
| 5,262,055 | 11/1993 | Bae et al. | 210/645 |
| 5,308,701 | 5/1994 | Cohen et al. | 428/402.22 |
| 5,387,237 | 2/1995 | Fournier et al. | 623/11 |
| 5,559,022 | 9/1996 | Naughton et al. | 424/93.21 |

OTHER PUBLICATIONS

Sarraf et al., American Journal of Pathology 145(5): 1114–1126 (Nov. 1994).
Sirica et al., American Journal of Pathology 120(1): 67–78 (1985) (Abstract).
Baumgardner, G., et al., "Cell Subsets Responding to Purified Hepatocytes and Evidence of Indirect Recognition of Hepatocyte Major Histocompatability Complex I Class Antigen," *Transplantation*, vol. 53, No. 4, 857–862 (1992).
DiBerardino, M., et al., "Activation of Dormant Genes in Specialized Cells," *Science*, vol. 224, 946–952 (1984).
Evarts, R., et al., "In Vivo Differentiation of Rat Liver Oval Cells into Hepatocytes", *Cancer Research*, vol. 49, 1541–1547 (1989).
Factor, V., et al., "Origin and Fate of Oval Cells in Dipin–Induced Hepatocarcinogenesis in the Mouse," *American Journal of Pathology*, vol. 145, No. 2, 409–422 (1994).
Faris , R., et al., "Isolation, Propagation, and Characterization of Rat Liver Serosal Mesothelial Cells," *American Journal of Pathology*, vol. 145, No. 6, 1432–1443 (1994).
Fausto, N., "Hepatocyte Differentiation and Liver Progenitor Cells," *Current Opinion in Cell Biology*, vol. 2, 1036–1042 (1990).
Fisher, M., "Neuronal Influence on Glial Enzyme Expression: Evidence from Mutant Mouse Cerebella," *PNAS*, vol. 81, 4414–4418 (1984).
Gurdon, J.B., "The Generation of Diversity and Pattern in Animal Development," *Cell*, vol. 68, 185–199 (1992).
Kay, M., et al., "Expression of Human $\alpha_1$–antitrypsin in Dogs After Autologous Transplantation of Retroviral Transduced Hepatocytes," *PNAS*, vol. 89, 89–93 (1992).
Langer, R., et al., "Tissue Engineering," *Science*, vol. 260, 920–926 (1993).
Li, Q., et al., "Assesment of Recombinant Adenoviral Vectros for Hepatic Gene Therapy," *Human Gene Therapy*, vol. 4, 403–409 (1993).
Nagy, P., et al., "Expression of Hepatic Transcription Factors During Liver Deveolpment and Oval Cell Differentiation," *The Journal of Cell Biology*, vol. 126, No. 1, 223–233(1994).
Pack, R., et al., "Isolation, Biochemical Characterization, Long–term Culture, and Phenotype Modulation of Oval Cells From Carcinogen–Fed Rats," *Experimental Cell Research*, vol. 204, 198–209 (1993).
Rao, M., et al., "Role of Periductal and Ductular Epithelial Cells of the Adult Rat Pancreas in Pancreatic Hepatocyte Lineage," *American Journal of Pathology*, vol. 134, No. 5, 1069–1086 (1989).
Sarraf, C., et al., "cell Behavior in the Acetylaminofluorene –Treated Regenerating Rat Liver," *American Journal of Pathology*, vol. 145, No. 5, 1114–1126 (1994).
Sell, S., "Is There a Liver Stem Cell?" *Cancer Research*, vol. 50, 3811–3815 (1990).
Shiojiri N., et al., "Cell Lineages and Oval Cell Progenitors in Rat Liver Development," *Cancer Research*, vol. 51, 2611–2620 (1991).
Sigal, S., et al., "Characterization and Enrichment of Fetal Rat Hepatoblasts by Immunoadsorption (Panning) and Fluorescence–activated Cell Sorting," *Hepatology*, vol. 19, No. 4, 999–1006 (1994).
Sullivan, S., et al., "Biohybrid Artifical Pancreas: Long–Term Implantation Studies in Diabetic, Pancreatectomized Dogs," *Science*, vol. 252, 718–721 (1993).
Teitelman, G., "On the Origin of Pancreatic Endocrine Cells, Proliferation and Neoplastic Transformation," *Tumor Biology*, vol. 14, 167–173 (1993).
Teitelman, G., "Precursor Cells of Mouse Endocrine Pancreas Coexpress Insulin, Glucagon and the Neuronal Proteins Tyrosine Hydoxylase and Neuropeptide Y, but not Pancreatic Polypeptide," *Development*, vol. 118, 1031–1039 (1993).
Terada, T. and Nakanuma, Y., "Development of Human Peribillary Capillary Plexus: A Lectin–Histochemical and Immunohistochemical Study," *Hepatology*, vol. 18, No. 3, 529–536 (1993).
Wetts, R., and Fraser, S., "Multipotent Precursors Can Give Rise to all Major Cell Types of the Frog Retina," *Science*, vol. 239, 1142–1144 (1988).
Dabeva, M. et al., "Models for Hepatic Progenitor Cell Activation," *Proceedings of the Society for Experimental Biology and Medicine*, vol. 204, No. 3, 242–252 (1993).

*Primary Examiner*—Jean C. Witz
*Attorney, Agent, or Firm*—Matthew P. Vincent; Beth E. Arnold; Foley, Hoag & Eliot LLP

[57] ABSTRACT

The present invention relates to a substantially pure population of viable bile duct progenitor cells, and methods for isolating such cells. The present invention further concerns certain therapeutic uses for such progenitor cells, and their progeny.

16 Claims, 2 Drawing Sheets

METHOD OF ISOLATING BILE DUCT PROGENITOR CELLS

BACKGROUND OF THE INVENTION

During the early stages of embryogenesis cells are totipotent and are capable of multidirectional differentiation. As development proceeds, the totipotent cells become determined and committed to differentiate into a given specialized cell type. Final differentiation is associated with the acquisition of specialized cell functions. Thus, the differentiated somatic cells maintain their specialized features throughout the life span of the organism, probably through sustained interactions between the genome and its microenvironment and cell—cell interactions (DiBerardino et al., 1984, *Science* 224:946–952; Wetts and Fraser, 1988, *Science* 239:1142–1144; Fisher, 1984, *PNAS* 81:4414–4418).

Because of the tremendous potential of progenitor cells to differentiate into distinct lineages, there has always existed a need for a continuous source of these isolated pluripotent progenitor cells. The pluripotent progenitor cells could be extremely useful in the treatment of different disorders that are characterized by insufficient or abnormal functioning of the fully differentiated cells in a given organ, as for example in the human pancreas or liver.

SUMMARY OF THE INVENTION

The present invention relates to substantially pure preparations of viable progenitor cells, and methods for isolating such cells. The present invention further concerns certain uses for such progenitor cells, and their progeny.

In general, the invention features a cellular composition including, as the cellular component, a substantially pure population of viable bile duct progenitor cells which progenitor cells are capable of proliferation in a culture medium. In a preferred embodiment, the cellular composition has fewer than about 20%, more preferably fewer than about 10%, most preferably fewer than about 5% of lineage committed cells.

In general, the progenitor cells of the present invention are proliferative cells which can differentiate into cells making up the tissues of the gut, e.g., the liver, pancreas, gallbladder, intestines, etc. That is, the progenitor cells can give rise to differentiated cells of hepatic, pancreatic, gallbladder or intestinal lineages. In preferred embodiments, the subject progenitor cells are pluripotent, e.g., the progenitor cells are capable of differentiating into two or more distinct lineages.

In one embodiment, the progenitor cells of the present invention are characterized by an ability for self-regeneration in a culture medium and differentiation to pancreatic lineages.

In a preferred embodiment, the progenitor cells are inducible to differentiate into pancreatic islet cells, e.g., β islet cells, α islet cells, δ islet cells, or φ islet cells.

In another embodiment, the invention features progenitor cells, such as may be obtained from a non-hepatic bile duct according to the present invention, which are characterized by an ability to differentiate (e.g., by induction) into hepatocytes when maintained in culture.

In yet another embodiment, the invention features a pharmaceutical composition including as the cellular component, a substantially pure population of viable bile duct progenitor cells, which progenitor cells are capable of proliferation in a culture medium.

In general, the preferred progenitor cells will be of mammalian origin, e.g., cells isolated from a primate such as a human, from a miniature swine, or from a transgenic mammal, or are the cell culture progeny of such cells.

In preferred embodiments, the subject progenitor cells can be maintained in cell/tissue culture for at least about 7 days, more preferably for at least about 14 days, most preferably for at least about 21 days or longer.

In another aspect, the invention features a cellular composition comprising, as a cellular population, at least 75% (though more preferably at least 80, 90 or 95%) progenitor cells isolated from a bile duct and capable of self-regeneration in a culture medium.

In yet another aspect, the invention features, a cellular composition consisting essentially of, as the cellular population, viable non-hepatic duct progenitor cells capable of self-regeneration in a culture medium and differentiation to members of the hepatic, pancreatic and gallbladder lineages. For instance, in certain embodiments the progenitor cells are isolated from cystic duct explants, pancreatic duct explants, common bile duct explants, or are the cell culture progeny of such cells.

Another aspect of the invention features a method for isolating progenitor cells from a bile duct. In general, the method provides for culturing an isolated population of cells having a microarchitecture of a mammalian bile duct, e.g. a micro-organ explant in which the original epithelial-mesenchymal microarchitecture is maintained, wherein the dimensions of the explant provide the isolated population of cells as maintainable in culture for at least twenty-four hours, and includes in the population of cells at least one progenitor cell which can proliferate under such culture conditions. The cultured cell population is contacted with an agent, e.g., a mitogenic agent such as a growth factor, which agent causes proliferation of progenitor cells in the cultured population. Subsequently, progenitor cells from the explant that proliferate in response to the agent are isolated, such as by direct mechanical separation of newly emerging buds from the rest of the explant or by dissolution of all or a portion of the explant and subsequent isolation of the progenitor cell population.

In another preferred embodiment, the agent is a growth factor, e.g., the growth factor is selected from a group consisting of IGF, TGF, FGF, EGF, HGF, or VEGF.

In yet another preferred embodiment, the progenitor cells isolated are pancreatic progenitor cells or hepatic progenitor cells.

In another preferred embodiment, the population of cells is cultured in a medium deficient in biological extracts, e.g., deficient in serum.

In a preferred embodiment, the bile duct is a common bile duct.

In another aspect, the invention features, a method for screening a compound for ability to modulate one of growth, proliferation, and/or differentiation of progenitor cells obtained from a bile duct, including: (i) establishing an isolated population of cells having a microarchitecture of a mammalian bile duct, e.g., a micro-organ explant in which the original epithelial-mesenchymal microarchitecture is maintained, wherein the dimensions of the explant provide the isolated population of cells as maintainable in culture for at least twenty-four hours, and includes at least one progenitor cell which has the ability to proliferate in the culture; (ii) contacting the population of cells with a test compound; and (iii) detecting one of growth, proliferation, and/or differentiation of the progenitor cells in the population, wherein a statistically significant change in the extent of one of growth, proliferation, and/or differentiation in the presence of the test compound relative to the extent of one of growth, proliferation, and/or differentiation in the absence of the test compound indicates the ability of the test compound to modulate one of the growth, proliferation, and/or differentiation.

In another aspect, the invention features, a method for treating a disorder characterized by insufficient insulin activity, in a subject, including introducing into the subject a pharmaceutical composition including pancreatic progenitor cells, or differentiated cells arising therefrom, and a pharmaceutically acceptable carrier.

In a preferred embodiment the subject is a mammal, e.g., a primate, e.g, a human.

In another preferred embodiment the disorder is an insulin dependent diabetes, e.g, type I diabetes.

In yet another preferred embodiment, the pancreatic progenitor cells are induced to differentiate into pancreatic islet cells, e.g., β islet cells, α islet cells, δ islet cells, or φ islet cells, subsequent to being introduced into the subject. Preferably, the pancreatic progenitors cells are induced to differentiate into pancreatic islet, e.g., β islet cells, α islet cells, δ islet cells, or φ islet cells, in culture prior to introduction into the subject.

In another aspect, the invention features, a method for treating a disorder characterized by insufficient liver function, in a subject, comprising introducing into the subject a pharmaceutical composition including hepatic progenitor cells and a pharmaceutically acceptable carrier.

In a preferred embodiment, the subject is a mammal, e.g., a primate, e.g., a human.

In another preferred embodiment the disorder is selected from the group consisting of cirrhosis, hepatitis B, hepatitis C, sepsis, or ELAD. In yet another preferred embodiment, the hepatic progenitor cells are induced to differentiate into hepatocytes subsequent to being introduced into the subject. Preferably, the hepatic progenitors cells are induced to differentiate into hepatocytes in culture prior to introduction into the subject.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Vucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

Other features and advantages of the invention will be apparent from the following detailed description, and from the claims.

DETAILED DESCRIPTION OF THE DRAWINGS

FIG. 1 is a graph depicting average number of BrdU positive nuclei in a common bile duct explant, 24 hours after administration of a growth factor. Growth factors, EGF, TGF-α, and basic FGF (bFGF) were administered in three doses: 1 ng/ml, 10 ng/ml and 100 ng/ml. DMEM minimal media was used as a control. Average fluorescence intensity was determined based on the number of positive nuclei.

DETAILED DESCRIPTION OF THE INVENTION

Figure 1:
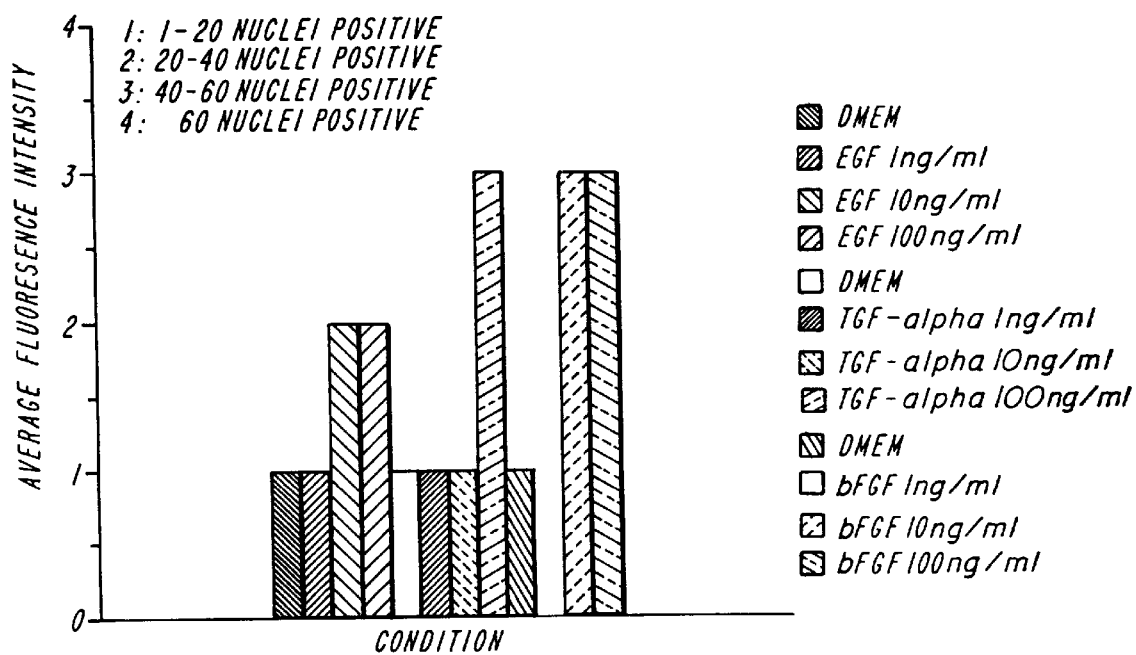

Ability to isolate distinct populations of progenitor cells has been an important problem in modern biology. It can be easily envisioned that such isolated pluripotent progenitor cells could be very useful for treatment of various disorders associated with loss or abnormal functioning of fully differentiated cells in a given organ. For example, the ability to introduce isolated progenitor cells capable of subsequent differentiation, either in culture or when introduced into a subject, into functional β islet cells, would have important implications for the treatment of insulin-dependent diabetes. In the same manner, the ability to deliver purified hepatic progenitor cells, having the ability to differentiate into mature hepatocytes, could be potentially useful in the process of liver regeneration or for treatment of disorders characterized by insufficient liver function. To date, there is not apparent reliable source of purified populations of progenitor cells from gut tissue capable of further differentiation into distinct pancreatic, hepatic, gallbladder, or intestinal lineages, either in culture or when introduced into a subject.

Accordingly, certain aspects of the present invention relate to isolated populations of progenitor cells capable of subsequent differentiation to distinct pancreatic, hepatic, gallbladder, or intestinal lineages, methods for isolating such cells and therapeutic uses for such cells.

For convenience, certain terms employed in the specification, examples, and appended claims are collected here.

The term "culture medium" is recognized in the art, and refers generally to any substance or preparation used for the cultivation of living cells. Accordingly, a "tissue culture" refers to the maintenance or growth of tissue, e.g., explants of organ primordia or of an adult organ in vitro so as to preserve its architecture and function. A "cell culture" refers to a growth of cells in vitro; although the cells proliferate they do not organize into tissue per se.

Tissue and cell culture preparations of the subject microorgan explants and amplified progenitor cell populations can take on a variey of formats. For instance, a "suspension culture" refers to a culture in which cells multiply while suspended in a suitable medium. Likewise, a "continuous flow culture" refers to the the cultivation of cells or ductal explants in a continuous flow of fresh medium to maintain cell growth, e.g. viablity. The term "conditioned media" refers to the supernatant, e.g. free of the cultured cells/tissue, resulting after a period of time in contact with the cultured cells such that the media has been altered to include certain paracrine and/or autocrine factors produced by the cells and secreted into the culture.

The terms "explant" and "micro-organ explant" refer to a portion of an organ taken from the body and grown in an artificial medium.

The term "tissue" refers to a group or layer of similarly specialized cells which together perform certain special functions.

The term "organ" refers to two or more adjacent layers of tissue, which layers of tissue maintain some form of cell—cell and/or cell-matrix interaction to form a microarchitecture.

The term "lineage committed cell" refers to a progenitor cell that is no longer pluripotent but has been induce to differentiate into a specific cell type, e.g., a pancreatic, hepatic or intestinal cell.

The term "progenitor cell" refers to an undifferentiated cell which is capable of proliferation and giving rise to more progenitor cells having the ability to generate a large number of mother cells that can in turn give rise to differentiated, or differentiable daughter cells. As used herein, the term "progenitor cell" is also intended to encompass a cell which is sometimes referred to in the art as a "stem cell". In a preferred embodiment, the term "progenitor cell" refers to a generalized mother cell whose descendants (progeny) specialize, often in different directions, by differentiation, e.g., by acquiring completely individual characters, as occurs in progressive diversification of embryonic cells and tissues. A "bile duct progenitor cells" refers to progenitor cells arising in tissue of a bile duct and giving rise to such differentiated progeny as, for example, hepatic, pancreatic, intestinal or gallbladder lineages.

As used herein the term "bile duct" refers to an intricate system of ducts, e.g., generally tubular structures used for secretion, either neonatal or adult. The term includes the hepatic duct, cystic duct, and pancreatic duct. The term "pancreatic duct" includes the accessory pancreatic duct, dorsal pancreatic duct, main pancreatic duct and ventral pancreatic duct. The term bile duct also encompasses the common bile duct. The main function of the bile duct is to allow bile and other materials to drain from these organs and enter the gastrointestinal tract.

As used herein the term "common bile duct" refers to a region of the bile duct, either adult or neonatal, originating from the liver bile canaliculi and extending down to the papilla of Vater at the duodenal junction. The common bile duct is continuous with hepatic, cystic and certain pancreatic ducts.

As used herein the term "non-hepatic bile duct" refers to that bile duct tissue which is not hepatic duct tissue, e.g., those portions of the common bile duct posterior to the hepatic duct. In addition, the term includes cystic and pancreatic ducts.

As used herein the term "substantially pure", with respect to progenitor cells, refers to a population of progenitor cells that is at least about 75%, preferably at least about 85%, more preferably at least about 90%, and most preferably at least about 95% pure, with respect to progenitor cells making up a total cell population. Recast, the term "substantially pure" refers to a population of progenitor cell of the present invention that contain fewer than about 20%, more preferably fewer than about 10%, most preferably fewer than about 5%, of lineage committed cells in the original unamplified and isolated population prior to subsequent culturing and amplification.

As used herein, the term "cellular composition" refers to a preparation of cells, which preparation may include, in addition to the cells, non-cellular components such as cell culture media, e.g. proteins, amino acids, nucleic acids, nucleotides, co-enzyme, anti-oxidants, metals and the like. Furthermore, the cellular composition can have components which do not affect the growth or viability of the cellular component, but which are used to provide the cells in a particular format, e.g., as polymeric matrix for encapsulation or a pharmaceutical preparation.

As used herein the term "animal" refers to mammals, preferably mammals such as humans. Likewise, a "patient" or "subject" to be treated by the method of the invention can mean either a human or non-human animal.

As described below, in a preferred embodiment, the progenitor cells of the present invention are pancreatic or hepatic progenitor cells. The term "pancreas" is art recognized, and refers generally to a large, elongated, racemose gland situated transversely behind the stomach, between the spleen and duodenum. The pancreatic exocrine function, e.g., external secretion, provides a source of digestive enzymes. Indeed, "pancreatin" refers to a substance from the pancreas containing enzymes, principally amylase, protease, and lipase, which substance is used as a digestive aid. The exocrine portion is composed of several serous cells surrounding a lumen. These cells synthesize and secrete digestive enzymes such as trypsinogen, chymotrypsinogen, carboxypeptidase, ribonuclease, deoxyribonuclease, triacylglycerol lipase, phospholipase $A_2$, elastase, and amylase.

The endocrine portion of the pancreas is composed of the islets of Langerhans. The islets of Langerhans appear as rounded clusters of cells embedded within the exocrine pancreas. Four different types of cells—$\alpha$, $\beta$, $\delta$, and $\phi$—have been identified in the islets. The $\alpha$ cells constitute about 20% of the cells found in pancreatic islets and produce the hormone glucagon. Glucagon acts on several tissues to make energy available in the intervals between feeding. In the liver, glucagon causes breakdown of glycogen and promotes gluconeogenesis from amino acid precursors. The $\delta$ cells produce somatostatin which acts in the pancreas to inhibit glucagon release and to decrease pancreatic exocrine secretion. The hormone pancreatic polypeptide is produced in the $\phi$ cells. This hormone inhibits pancreatic exocrine secretion of bicarbonate and enzymes, causes relaxation of the gallbladder, and decreases bile secretion. The most abundant cell in the islets, constituting 60–80% of the cells, is the $\beta$ cell, which produces insulin. Insulin is known to cause the storage of excess nutrients arising during and shortly after feeding. The major target organs for insulin are the liver, muscle, and fat-organs specialized for storage of energy.

The term "pancreatic progenitor cell" refers to a cell which can differentiate into a cell of pancreatic lineage, e.g. a cell which can produce a hormone or enzyme normally produced by a pancreatic cell. For instance, a pancreatic progenitor cell may be caused to differentiate, at least partially, into $\alpha$, $\beta$, $\delta$, or $\phi$ islet cell, or a cell of exocrine fate. The pancreatic progenitor cells of the invention can also be cultured prior to administration to a subject under conditions which promote cell proliferation and differentiation. These conditions include culturing the cells to allow proliferation and confluence in vitro at which time the cells can be made to form pseudo islet-like aggregates or clusters and secrete insulin, glucagon, and somatostatin.

The term "liver" refers to the large, dark-red gland in the upper part of the abdomen on the right side, just beneath the diaphragm. Its manifold functions include storage and filtration of blood, secretion of bile, conversion of sugars into glycogen, and many other metabolic activities.

The liver is a gland that supplies bile to intestine. In adult vertebrates, this function is a minor one, but the liver originally arose as a digestive gland in lower chordates. Throughout the liver, a network of tiny tubules collects bile—a solution of salts, bilirubin (made when hemoglobin from red blood cells is broken down in liver), and fatty acids. Bile accumulates in the gall bladder, which empties into the small intestine by way of a duct. Bile has two functions in the intestine. First, it acts as a detergent, breaking fat into small globules that can be attacked by digestive enzymes. Second, and more important, bile salts aid in the absorption of lipids form the intestine; removal of the gall bladder sometimes causes difficulty with lipid absorption.

Digested food molecules absorbed into the bloodstream from the intestine pass directly to the liver by way of the hepatic portal vein. Before these molecules pass on into the rest of the body, the liver may change their concentration and even their chemical structure. The liver performs a vital role in detoxifying otherwise poisonous substances. In addition, it stores food molecules that reach it form the intestine, converts them biochemically, and releases them back into the blood at a controlled rate. For instance, the liver removes glucose from the blood under the influence of the hormone insulin and stores it as glycogen. When the level of glucose in the blood falls, the hormone glucagon causes the liver to break down glycogen and release glucose into the blood.

The liver also synthesizes many of the blood proteins (e.g., albumins) and releases them into the blood when they are needed. In addition, the liver converts nitrogenous wastes into the form of urea for excretion by the kidneys. With the kidneys, the liver is vital in regulating what the blood contains when it reaches all the other organs of the body. Because the liver is the body's major organ for making all these biochemical adjustments, severe liver damage or loss of the liver is rapidly fatal.

The term "hepatic progenitor cell" as used herein refers to a cell which can differentiate in a cell of hepatic lineage, such a liver parenchymal cell, e.g., a hepatocyte. Hepatocytes are some of the most versatile cells in the body. Hepatocytes have both endocrine and exocrine functions, and synthesize and accumulate certain substance, detoxify others, and secrete others to perform enzymatic, transport, or hormonal activities. The main activities of liver cells include bile secretion, regulation of carbohydrate, lipid, and protein metabolism, storage of substances important in metabolism, degradation and secretion of hormones, and transformation and excretion of drugs and toxins. The hepatic progenitor cells of the invention can also be cultured prior to administration to a subject under conditions which promote cell proliferation and differentiation.

Certain terms being set out above, it is noted that one aspect of the present invention features a method for isolating progenitor cells from micro-organ explants, e.g., ductal tissue explants. A salient feature of the subject method concerns the use of defined explants as sources from which discrete progenitor cell populations can be amplified. For instance, as described below, the progenitor source ductal tissue explants preferably are derived with dimensions that allow the tissue to maintain its microarchitecture and biological function for prolonged periods of time in culture, e.g., the dimensions of the explant preserve the normal tissue architecture and at least a portion of the normal tissue function that is present in vivo. Such tissue explants can be maintained, for instance, in minimal culture media for extended periods of time (e.g., for 21 days or longer) and can be contacted with different factors. Accordingly, carefully defined conditions can be acquired in the culture so as selectively activate discrete populations of cells in the tissue explant. The progenitor cells of the present invention can be amplified, and subsequently isolated from the explant, based on a proliferative response upon, for example, addition of defined growth factors or biological extracts to the culture.

In general, the method of the present invention can be used to isolate progenitor cells from a bile duct explant by steps beginning with the culturing of an isolated population of cells having a microarchitecture of a mammalian bile duct, e.g. a micro-organ explant in which the original epithelial-mesenchymal microarchitecture of the originating duct is maintained, wherein the dimensions of the explant provide the isolated population of cells as maintainable in culture for at least twenty-four hours, and includes in the population of cells at least one progenitor cell which can proliferate under such culture conditions. The explant is contacted with an agent, e.g., a mitogenic agent such as a growth factor or other biological extract, which agent causes proliferation of progenitor cells in the cultured population. Subsequently, progenitor cells from the explant that proliferate in response to the agent are isolated, such as by direct mechanical separation from the rest of the explant or by dissolution of all or a portion of the explant and subsequent isolation of the progenitor cell population.

In a illustrative embodiment, the size of the particular ductal explant will depend largely on (i) the availability of tissue, and (ii) a need for similar availability of nutrients to all cells in the tissue by diffusion. In a preferred embodiment, the ductal tissue explant is selected to provide diffusion of adequate nutrients and $O_2$ to every cell in a three dimensional organ. Accordingly, the size of the explant is determined by the requirement for a minimum level of accessibility to each cell absent specialized delivery structures or synthetic substrates.

A salient feature of the micro-organ cultures used to in the subject methods, according to the invention, is the ability to preserve the cellular microenvironment found in vivo for a ductal tissue. The invention is based, in part, upon the discovery that under certain circumstances growth of cells of both a stromal and epithelial layer, provided together in the same explant, will sustain active proliferation of cells of each layer. Moreover, the cell—cell and cell-matrix interactions provided in the explant itself are sufficient to support cellular homeostasis, e.g., maturation, differentiation and segregation of cells in the explant culture, thereby sustaining the microarchetecture and function of the explant for prolonged periods of time.

An example of physical contact between a cell and a noncellular substrate (matrix) is the physical contact between an epithelial cell and its basal lamina. An example of physical contact between a cell and another cell includes actual physical contact maintained by, for example, intercellular cell junctions such as gap junctions and tight junctions. Examples of functional contact between one cell and another cell includes electrical or chemical communication between cells. In addition, many cells communicate with other cells via chemical messages, e.g., hormones, which either diffuse locally (paracrine signalling and autocrine signalling), or are transported by the vascular system to more remote locations (endocrine signalling).

Not wishing to be bound by any particular theory, this microarchitecture of the ductal explants can be extremely important for the maintenance of the explant in minimal media, e.g., without exogneous sources of serum or growth factors, as the ductal explants can apparently be sustained in such minimal media by paracrine factors resulting from specific cellular interactions within the sample. Moreover, there is also a possibility that certain growth factors might act indirectly by activating cells, other than progenitor cells, to produce mitogenic factors that subsequently cause proliferation of progenitor cells within the explant. Accordingly, the ductal explants are derived such that they comprise both an epithelial layer and a stromal layer, and maintain, in vitro, the physical and/or fucntional interaction between these two component of the explant.

However, the phrase "maintain, in vitro, the physical and/or functional interaction" is not intended to exclude an isolated population of cells in which at least one cell develops physical and/or functional contact with at least one cell or noncellular substance with which it is not in physical and/or functional contact in vivo. An example of such a development is of course proliferation of at least one cell of the isolated population of cells.

As emphasized through the present application, the micro-organ cultures used to prepare progenitor cells according to the invention preserve the normal tissue architecture that is present in vivo, e.g., the original epithelial-mesenchymal organization. In preferred embodiments, the populations of cells of the ductal explants are grouped in a manner that preserves the natural affinity of one cell to another, e.g., to preserve layers of different cells present in explant. Such an association facilitates intercellular communication. Many types of communication takes place among animal cells. This is particularly important in differentiating cells where induction is defined as the interaction between one (inducing) and another (responding) tissue or cell, as a result of which the responding cells undergo a change in the direction of differentiation. Moreover, inductive interactions occur in embryonic and adult cells and can act to establish and maintain morphogenetic patterns as well as induce differentiation (Gurdon (1992) Cell 68: 185–199). Accordingly, an exemplary micro-organ cultures prepared in accordance to use in the progenitor amplification method of the invention are described in Example I, and include a epithelial and mesenchymal cells grouped in a manner that includes a plurality of layers so as to preserve the natural affinity and interaction of one cell to another in and between each layer.

In addition to isolating a ductal explant which retains the cell—cell and cell-matrix architecture of the originating duct, the dimensions of the explant are important to the viability of the cells therein, e.g., where the micro-organ culture is intended to be sustained for prolonged periods of time, e.g., 7–21 days or longer. Accordingly, the dimensions of the explant are selected to provide diffusion of adequate nutrients and gases (e.g, $O_2$, $CO_2$, etc) to every cell in the three dimensional micro-organ explant, as well as diffusion of cellular waste out of the explant so as to minimize cellular toxicity and concommitant death due to localization of the waste in the micro-organ. Thus, in addition to the requirement of both epithelial and mesenchymal components, the size of the explant is determined by the requirement for a minimum level of accessibility to each cell in the absence specialized delivery structures or synthetic substrates. As described herein, this accessibility can be maintained if Aleph, an index calculated from the thickness and the width of the explant, is at least greater than approximately 1.5 $mm^{-1}$. As used herein, a surface to area index, "Aleph" is defined as $$Aleph = \frac{1}{x} + \frac{1}{a} > 1.5 mm^{-1};$$

wherein x=radial thickness and a=the axial length of the duct explant in millimeters. Accordingly, the present invention provides that the surface area to volume index of the tissue explant is maintained within a selected range. This selected range of surface area to volume indice provides the cells access to nutrients and to avenues of waste disposal by diffusion in a manner similar to cells of the in vivo organ from which the explant originated.

Examples of Aleph are provided in Table I wherein, for example, an explant having a thickness (x) of 0.1 mm and a width (a) of 1 mm would have an Aleph index of 11. In another instance, if x=0.3 mm and a=4 mm, the Aleph is 3.58 $mm^{-1}$. To further illustrate, Applicant has observed that when x is varied and a is constant at 4 mm, the proliferative activity of cells in a cultured explant is substantially reduced as the thickness of the explant increases. Accordingly, at 900 $\mu m$ thickness, the number of proliferating cells in a micro-organ culture was found to about 10 fold less than in tissue from a similar source having a thickness of 300 $\mu m$. The Aleph index for a tissue having a thickness of 900 $\mu m$ is 1.36 $mm^{-1}$, below the minimum described herein whereas the Aleph index for tissue having a thickness of 300 $\mu m$ is 3.58 $mm^{-1}$ which is well within the range defined herein.

TABLE I

Different values for the surface area to volume ratio index "Aleph", as a function of a (width) and x (thickness) in $mm^{-1}$

| | | ←Radial Length→ | | | | |
|---|---|---|---|---|---|---|
| x (mm) | a = 1 mm | a = 2 mm | a = 3 mm | a = 4 mm | a = 5 mm | |
| ↑ | 0.1 | 11 | 10.5 | 10.33 | 10.25 | 10.2 | ↑ |
| thickness | 0.2 | 6 | 5.5 | 5.33 | 5.25 | 5.2 | Aleph |
| ↓ | 0.3 | 4.3 | 3.83 | 3.67 | 3.58 | 3.53 | ↓ |
| | 0.4 | 3.5 | 3 | 2.83 | 2.75 | 2.7 | |
| | 0.5 | 3 | 2.5 | 2.33 | 2.25 | 2.2 | |
| | 0.6 | 2.66 | 2.16 | 2 | 1.91 | 1.87 | |
| | 0.7 | 2.4 | 1.92 | 1.76 | 1.68 | 1.63 | |
| | 0.8 | 2.25 | 1.75 | 1.58 | 1.5 | 1.45 | |
| | 0.9 | 2.11 | 1.61 | 1.44 | 1.36 | 1.31 | |
| | 1 | 2 | 1.5 | 1.33 | 1.25 | 1.2 | |
| | 1.2 | 1.83 | 1.3 | 1.16 | 1.08 | 1.03 | |
| | 1.3 | 1.77 | 1.26 | 1.1 | 1.02 | 0.96 | |
| | 1.6 | 1.625 | 1.13 | 0.96 | 0.88 | 0.83 | |
| | 2 | 1.5 | 1 | 0.83 | 0.75 | 0.7 | |

Again, not wishing to be bound by any particular theory, a number of factors provided by the three-dimensional culture system may contribute to its success inthe subject method of activating progenitor cell populations:

(a) The appropriate choice of the explant size, vis-à-vis the use of the above Aleph calculations, three-dimensional matrix provides appropriate surface area to volume ratio for adequate diffusion of nutrients to all cells of the explant, and adequate diffusion of cellular waste away from all cells in the explant.

(b) Because of the three-dimensionality of the matrix, various cells continue to actively grow, in contrast to cells in monolayer cultures, which grow to confluence, exhibit contact inhibition, and cease to grow and divide. The elaboration of growth and regulatory factors by replicating cells of the explant may be partially responsible for stimulating proliferation and regulating differentiation of cells in culture.

(c) The three-dimensional matrix retains a spatial distribution of cellular elements, e.g., the epithelial-mesenchymal micoarchitecture, which closely approximates that found in the counterpart tissue in vivo.

(d) The cell—cell and cell-matrix interactions may allow the establishment of localized microenvironments conducive to cellular induction and/or maturation. It has been recognized that maintenace of a differentiated cellular phenotype requires not only growth/differentiation factors but also the appropriate cellular interactions. The present invention effectively mimics the microenvironment. Accordingly, the micro-organ preserves interactions which may be required to maintain the cells supporting the progenitor cells, the cells (if any) providing inductive signals to the progenitor cells, and the progenitor cells themselves.

To further illustrate, Example 1 demonstrates that micro-organ explants, in which the original epithelial-mesenchymal microarchitecture of the common bile duct are prepared by transverse sectioning of the duct every 300 $\mu$m, can be maintained in simple media (DMEM) for several weeks and can be used to isolate progenitor cells of the present invention by growth induction upon contact with certain growth factors.

There are a large number of tissue culture media that exist for culturing tissue from animals. Some of these are complex and some are simple. While it is expected that the ductal explants may grow in complex media, it will generally be preferred that the explants be maintained in a simple medium, such as Dulbecco's Minimal Essential Media (DMEM), in order to effect more precise control over the activation of certain progenitor populations in the explant. Furthermore, although the cultures may be grown in a media containing sera or other biological extracts such as pituitary extract, it has been demonstrated that neither sera nor any other biological extract is required for explants derived according to the above considerations (see U.S. Ser. No. 08/341,409,). Moreover, the explants can be maintained in the absence of sera for extended periods of time. In preferred embodiments of the invention, the growth factors or other mitogenic agents are not included in the primary media for maintenance of the cultures in vitro, but are used subsequently to cause proliferation of distinct populations of progenitor cells. See the appended examples.

The tissue explants may be maintained in any suitable culture vessel, such as a 24 or 96 well microplate, and may be maintained under typical culture conditions for cells isolated from the same animal, e.g., such as 37° C. in 5% $CO_2$. The cultures may be shaken for improved aeration, the speed of shaking being, for example, 12 rpm.

In order to isolate progenitor cells from the ductal explants, it will generally be desirable to contact the explant with an agent which causes proliferation of one or more populations of progenitor cells in the explant. For instance, a mitogen, e.g., a substance that induces mitosis and cell transformation, can be used to detect a progenitor cell population in the explant, and where desirable, to cause the amplification of that population. To illustrate, a purified or semi-purifed preparation of a growth factor can be applied to the culture. Induction of progenitor cells which respond to the applied growth factor can be detected by proliferation of the progenitor cells. However, as described below, amplification of the population need not occur to a large extent in order to use certain techniques for isolating the responsive population.

Methods of measuring cell proliferation are well known in the art and most commonly include determining DNA synthesis characteristic of cell replication. There are numerous methods in the art for measuring DNA synthesis, any of which may be used according to the invention. In an embodiment of the invention, DNA synthesis has been determined using a radioactive label ($^3$H-thymidine) or labeled nucleotide analogues (BrdU) for detection by immunofluorescence.

However, in addition to measuring DNA synthesis, morphological changes can be, and preferably will be, relied on as the basis for isolating responsive progenitor cell populations. For instance, as described in the appended examples, we have observed that certain growth factors cause amplification of progenitor cells in ductal explants so as to form structures that can be easily detected by the naked eye or microscopy. In an exemplary embodiment, those progenitor cells which respond to growth factors by proliferation and subsequent formation of outgrowths from the explant, e.g., buds or blebs, can be easily detected. In another illustrative embodiment, other structural changes, e.g., changes in optical density of proliferating cells, can be detected via contrast microscopy.

Various techniques may be employed to isolate the activated progenitor cells of treated explant. Preferred isolation procedures for progenitor cells are the ones that result in as little cell death as possible. For example, the activated progenitor cells can be removed from the explant sample by mechanical means, e.g., mechanically sheared off with a pipette. In other instances, it will be possible to dissociate the progenitor cells from the entire explant, or sub-portion thereof, e.g., by enzymatic digestion of the explant, followed by isolation of the activated progenitor cell population based on specific cellular markers, e.g., using affinity separation techniques or fluorescence activated cell sorting (FACS).

To further illustrate, the examples below demonstrate that ductal explants contain growth factor responsive progenitor cell types. It is further demonstrated that different growth factors can induce/amplify distinct populations of progenitor cells within the ductal tissue explant to proliferate. This indicates the presence of specific growth factor receptors on the surface of distinct progenitor cell populations. This is important because the expression of these receptors marks the progenitor cell populations of interest. Monoclonal antibodies are particularly useful for identifying markers (surface membrane proteins, e.g., receptors) associated with particular cell lineages and/or stages of differentiation. Procedures for separation of the subject progenitor cell may include magnetic separation, using antibody coated magnetic beads, affinity chromatography, and "panning" with antibody attached to a solid matrix, e.g., plate, or other convenient technique. Techniques providing accurate separation include fluorescence activated cell sorting, which can have varying degrees of sophistication, e.g., a plurality of color channels, low angle and obtuse light scattering detecting channels, impedance channels, etc.

Conveniently, the antibodies may be conjugated with markers, such as magnetic beads, which allow for direct separation, biotin, which can be removed with avidin or streptavidin bound to a support, fluorochromes, which can be used with a fluorescence activated cell sorter, or the like, to allow for ease of separation of the particular cell type. Any technique may be employed which is not unduly detrimental to the viability of the cells.

In an illustrative embodiment, some of the antibodies for growth factor receptors that exist on the subject progenitor cells are commercially available (e.g., antibodies for EGF receptors and FGF receptors), and for other growth factor receptors, antibodies can be made by methods well known to one skilled in the art. In addition to using antibodies to isolate progenitor cells of interest, one skilled in the art can also use the growth factors themselves to label the cells, for example, to permit "panning" processes.

Upon isolation, the progenitor cells of the present invention can be further characterized in the following manner: responsiveness to growth factors, specific gene expression, antigenic markers on the surface of such cells, or basic morphology.

For example, extent of growth factor responsivity, e.g., the concentration range of growth factor to which they will respond to, the maximal and minimal responses, and to what other growth factors and conditions to which they might respond, can be used to characterize the subject progenitor cells.

Furthermore, the isolated progenitor cells can be characterized by the expression of genes known to mark the developing (i.e., stem or progenitor) cells for liver, pancreas, and intestine.

In an illustrative embodiment, the HNF transcription factor family, HNF1–4, are known to be expressed in various cell types at various times during liver development. ATBF1, a regulator of alphafetoprotein (AFP) gene expression (AFP is expressed early in liver development and is reexpressed in many liver carcinomas) has been postulated to be a transient marker of liver stem cells. The LIMM type homeobox genes are also known to be expressed during liver development. Therefore, expression of any of these genes can be used to further characterize the subject progenitor cells.

In another illustrative embodiment, the homeodomain type transcription factors IPF-1/IDX-1 (mouse/rat respectively) have recently been shown to mark different populations of the developing pancreas. Some LIM genes have also been shown to regulate insulin gene expression and would also be markers for protodifferentiated β islet cells.

In the intestine, even though there are not very many lineage specific transcription factors that have been mapped to the gut, the exception is the Hox B (homeobox genes) gene family (and possibly others) which are regional type markers rather than cell type specific, but which can be used to characterize progenitor cells originating form the specific region, e.g., the gut. Elastase is known to be any early marker of duodenal development and hence can be a candidate early marker for subject progenitor cells.

The subject progenitor cells can also be characterized on the basis of specific antigenic markers or other markers that may be expressed on the cell surface, e.g., integrins, lectins, gangliosides, or transporters, or on the basis of specific cellular morphology. All of these techniques are known and available to the one skilled in the art.

Once isolated and characterized, the subject progenitor cells can be cultured under conditions which allow further differentiation into specific cell lineages, e.g., hepatic, pancreatic, gallbladder, or intestinal lineages. This can be achieved through a paradigm of induction that can be developed. For example, the subject progenitor cells can be recombined with the corresponding embryonic tissue to see if the embryonic tissue can instruct the adult cells to codevelop and codifferentiate.

Furthermore, it has become apparent, from the prolonged viability of the explanted bile duct fragments in minimal media, that the tissues making up the ductal explants are themselves producing certain factors, e.g. paracrine and/or autocrine. Accordingly, such conditioned media generated by the explants in culture can be used to further maintain the progenitor cells in culture subsequent to isolation from the explant. The subject progenitor cells can be cultured in contact with the corresponding bile duct explant, or in the conditioned media produced by such explant.

In another preferred embodiment, the subject progenitor cells can be implanted into one of a number of regeneration models used in the art, e.g., partial pancreatectomy or streptozocin treatment of a host animal.

Accordingly, another aspect of the present invention pertains to the progeny of the subject progenitor cells, e.g. those cells which have been derived from the cells of the initial explant culture. Such progeny can include subsequent generations of progenitor cells, as well as lineage committed cells, e.g., hepatic, pancreatic or gallbladder cells generated by inducing differentiation of the subject progenitor cells after their isolation from the explant, e.g., induced in vitro.

Yet another aspect of the present invention concerns cellular compositions which include, as a cellular component, substantially pure preparations of the subject progenitor cells, or the progeny thereof. Cellular compositions of the present invention include not only substantially pure populations of the progenitor cells, but can also include cell culture components, e.g., culture media including amino acids, metals, coenzyme factors, as well as small populations of non-progenitor cells, e.g, some of which may arise by subsequent differentiation of isolated progenitor cells of the invention. Furthermore, other non-cellular components include those which render the cellular component suitable for support under particular circumstances, e.g., implantation, e.g., continuous culture.

As common methods of administering the progenitor cells of the present invention to subjects, particularly human subjects, which are described in detail herein, include injection or implantation of the cells into target sites in the subjects, the cells of the invention can be inserted into a delivery device which facilitates introduction by, injection or implantation, of the cells into the subjects. Such delivery devices include tubes, e.g., catheters, for injecting cells and fluids into the body of a recipient subject. In a preferred embodiment, the tubes additionally have a needle, e.g., a syringe, through which the cells of the invention can be introduced into the subject at a desired location. The progenitor cells of the invention can be inserted into such a delivery device, e.g., a syringe, in different forms. For example, the cells can be suspended in a solution or embedded in a support matrix when contained in such a delivery device. As used herein, the term "solution" includes a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is well known in the art. The solution is preferably sterile and fluid to the extent that easy syringability exists. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the invention can be prepared by incorporating progenitor cells as described herein in a pharmaceutically acceptable carrier or diluent and, as required, other ingredients enumerated above, followed by filtered sterilization.

Support matrices in which the progenitor cells can be incorporated or embedded include matrices which are recipient-compatible and which degrade into products which are not harmful to the recipient. Natural and/or synthetic biodegradable matrices are examples of such matrices.

Natural biodegradable matrices include plasma clots, e.g., derived from a mammal, and collagen matrices. Synthetic biodegradable matrices include synthetic polymers such as polyanhydrides, polyorthoesters, and polylactic acid. Other examples of synthetic polymers and methods of incorporating or embedding cells into these matrices are known in the art. See e.g., U.S. Pat. No. 4,298,002 and U.S. Pat. No. 5,308,701. These matrices provide support and protection for the fragile progenitor cells in vivo and are, therefore, the preferred form in which the progenitor cells are introduced into the recipient subjects.

The present invention also provides substantially pure progenitor cells which can be used therapeutically for treatment of various disorders associated with insufficient functioning of the pancreas or liver.

To illustrate, the subject progenitor cells can be used in the treatment of a variety of pancreatic disorders, both exocrine and endocrine. For instance, the progenitor cells can be used to produce populations of differentiated pancreatic cells for repair subsequent to partial pancreatectomy, e.g., excision of a portion of the pancreas. Likewise, such cell populations can be used to regenerate or replace pancreatic tissue loss due to, pancreatolysis, e.g., destruction of pancreatic tissue, such as pancreatitis, e.g., a condition due to autolysis of pancreatic tissue caused by escape of enzymes into the substance.

In an exemplary embodiment, the subject progenitor cells can be provided for patients suffering from any insulin-deficiency disorder. For instance, each year, over 728,000 new cases of diabetes are diagnosed and 150,000 Americans die from the disease and its complications; the total yearly cost in the United States is over 20 billion dollars (Langer et al. (1993) *Science* 260:920–926). Diabetes is characterized by pancreatic islet destruction or dysfunction leading to loss of glucose control. Diabetes mellitus is a metabolic disorder defined by the presence of chronically elevated levels of blood glucose (hyperglycemia). Insulin-dependent (Type 1) diabetes mellitus ("IDDM") results from an autoimmune-mediated destruction of the pancreatic β-cells with consequent loss of insulin production, which results in hyperglycemia. Type 1 diabetics require insulin replacement therapy to ensure survival. Non-insulin-dependent (Type 2) diabetes mellitus ("NIDDM") is initially characterized by hyperglycemia in the presence of higher-than-normal levels of plasma insulin (hyperinsulinemia). In Type 2 diabetes, tissue processes which control carbohydrate metabolism are believed to have decreased sensitivity to insulin. Progression of the Type 2 diabetic state is associated with increasing concentrations of blood glucose, and coupled with a relative decrease in the rate of glucose-induced insulin secretion.

The primary aim of treatment in both forms of diabetes mellitus is the same, namely, the reduction of blood glucose levels to as near normal as possible. Treatment of Type 1 diabetes involves administration of replacement doses of insulin. In contrast, treatment of Type 2 diabetes frequently does not require administration of insulin. For example, initial therapy of Type 2 diabetes may be based on diet and lifestyle changes augmented by therapy with oral hypoglycemic agents such as sulfonylurea. Insulin therapy may be required, however, especially in the later stages of the disease, to produce control of hyperglycemia in an attempt to minimize complications of the disease, which may arise from islet exhaustion.

More recently, tissue-engineering approaches to treatment have focused on transplanting healthy pancreatic islets, usually encapsulated in a membrane to avoid immune rejection. Three general approaches have been tested in animal models. In the first, a tubular membrane is coiled in a housing that contained islets. The membrane is connected to a polymer graph that in turn connects the device to blood vessels. By manipulation of the membrane permeability, so as to allow freediffusion of glucose and insulin back and forth through the membrane, yet block passage of antibodies and lymphocytes, normoglycemia was maintained in pancreatectomized animals treated with this device (Sullivan et al. (1991) *Science* 252:718).

In a second approach, hollow fibers containing islet cells were immobilized in the polysaccharide alginate. When the device was place intraperitoneally in diabetic animals, blood glucose levels were lowered and good tissue compatibility was observed (Lacey et al. (1991) *Science* 254:1782).

Finally, islets have been placed in microcapsules composed of alginate or polyacrylates. In some cases, animals treated with these microcapsules maintained normoglycemia for over two years (Lim et al. (1980) *Science* 210:908; O'Shea et al. (1984) *Biochim. Biochys. Acta.* 840:133; Sugamori et al. (1989) *Trans. Am. Soc. Artif. Intern. Organs* 35:791; Levesque et al. (1992) *Endocrinology* 130:644; and Lim et al. (1992) *Transplantation* 53:1180). However, all of these transplantation strategies require a large, reliable source of donor islets.

The pancreatic progenitor cells of the invention can be used for treatment of diabetes because they have the ability to differentiate into cells of pancreatic lineage, e.g., β islet cells. The progenitor cells of the invention can be cultured in vitro under conditions which can further induce these cells to differentiate into mature pancreatic cells, or they can undergo differentiation in vivo once introduced into a subject. Many methods for encapsulating cells are known in the art. For example, a source of β islet cells producing insulin is encapsulated in implantable hollow fibers. Such fibers can be pre-spun and subsequently loaded with the β islet cells (Aebischer et al. U.S. Pat. No. 4,892,538; Aebischer et al. U.S. Pat. No. 5,106,627; Hoffman et al. (1990) *Expt. Neurobiol.* 110:39–44; Jaeger et al. (1990) *Prog Brain Res.* 82:41–46; and Aebischer et al. (1991) *J Biomech. Eng.* 113:178–183), or can be co-extruded with a polymer which acts to form a polymeric coat about the β islet cells (Lim U.S. Pat. No. 4,391,909; Sefton U.S. Pat. No. 4,353,888; Sugamori et al. (1989) *Trans. Am. Artif Intern. Organs* 35:791–799; Sefton et al. (1987) *Biotehnol. Bioeng.* 29:1135–1143; and Aebischer et al. (1991) *Biomaterials* 12:50–55).

Moreover, in addition to providing a source of implantable cells, either in the form of the progenitor cell population of the differentiated progeny thereof, the subject cells can be used to produce cultures of pancreatic cells for production and purification of secreted factors. For instance, cultured cells can be provided as a source of insulin. Likewise, exocrine cultures can be provided as a source for pancreatin.

The liver is an organ that is vulnerable to a wide variety of metabolic, circulatory, toxic, microbial, and neoplastic insults, and is, therefore, one of the most frequently injured organs in the body. However, because the function of liver is very complex, synthetically recreating its function is practically impossible. One way of restoring liver function is by whole organ transplantation. Although transplantation of whole liver is often times successful it has plateaued at about 2200 transplants per year because of donor scarcity. Therefore, alternative treatments concentrate on manipulating the smallest functional unit of the liver, the individual hepatocyte.

In yet another embodiment, the subject progenitor cells, or their pogeny, can be used in the treatment various hepatic disorders. Vulnerable to a wide variety of metabolic, circulatory, toxic, microbial, and neoplastic insults, the liver is one of the most frequently injured organs in the body. In some instances, the disease is primarily localized in liver cells. For example, primary liver diseases include hereditary disorders such as Gilbert's Syndrome, Crigler-Najjar Syndrome (either Type I or Type II), Dubin Johnson Syndrome, familial hypercholesterolemia (FH), ornithine transcarbamoylase (OTC) deficiency, hereditary emphysema and hemophilia; viral infections such as hepatitis A, B, and non-A, non-B hepatitis; and hepatic malignancies such as hepatocellular carcinoma. Robbins, S. L. et al. (1984) Pathologic Basis of Disease (W. B. Saunders Company, Philadelphia) pp. 884–942. More often, the hepatic involvement is secondary, often to some of the most common diseases of man, such as cardiac decompensation, disseminated cancer, alcoholism, and extrahepatic infections. Robbins, S. L. et al. (1984) Pathologic Basis of Disease (W. B. Saunders Company, Philadelphia) pp. 884–942.

Whole liver transplantation, which is the current therapy for a variety of liver diseases, has been employed to successfully reconstitute LDL receptors in individuals with FH, thereby lowering serum cholesterol to normal levels. Whole liver transplantation, however, is limited by the scarcity of suitable donor organs. Li, Q. et al. (1993) *Human Gene Therapy* 4:403–409; Kay, M. A. et al. (1992) *Proc. Natl. Acad Sci.* 89:89–93. In addition to the difficulty in obtaining donor organs, the expense of liver transplantation, estimated at approximately $200,000 to $300,000 per procedure, prohibits its widespread application. Another unsolved problem is graft rejection. Foreign livers and liver cells are poorly tolerated by the recipient and are rapidly destroyed by the immune system in the absence of immunosuppressive drugs. Li, Q. et al. (1993) *Human Gene Therapy* 4:403–409; Bumgardner, G. L. et al. (1992) *Transplantation* 53:857–862. While immunosuppressive drugs may be used to prevent rejection, they also block desirable immune responses such as those against bacterial and viral infections, thereby placing the recipient at risk of infection.

The hepatic progenitor cells of the invention can be used for treatment of many liver disorders because they have the ability to differentiate into cells of hepatic lineage, e.g., hepatocytes. The progenitor cells of the invention can be cultured in vitro under conditions which can further induce these cells to differentiate into mature hepatocytes, or they can undergo differentiation in vivo once introduced into a subject. Many methods for encapsulating cells are known in the art, as has been described above for pancreatic cells. The hepatic progenitor cells can also be introduced directly into a subject, as they have the potential to induce liver regeneration.

Yet another aspect of the present invention provides methods for screening various compounds for their ability to modulate growth, proliferation or differentiation of distinct progenitor cell populations from bile duct tissue. A micro-organ explant that closely mimics the properties of a given set of tissue in vivo would have utility in screening assays in which compounds could be tested for their ability to modulate one of growth, proliferation or differentiation of progenitor cells in such tissue. Requirements of a reproducible model for screening might include consistency in the micro-architecture, e.g. epithelial-mesenchymal interactions, and nutritional environment in vitro, as well as prolonged viability and proliferation of cultures beyond 24 hours to observe threshold effects of compounds being screened. This level of consistency cannot be achieved in the presence of undefined media supplements such as sera or tissue extracts that vary between batches and cannot be adequately controlled. The dependence of a model on external growth supplements such as growth factors is also undesirable as growth factors or hormones may be included among the compounds to be tested.

In an illustrative embodiment, the ductal explants, which maintain their microarchitecture in culture, e.g., they preserve the normal epithelial-mesenchymal architecture that is present in vivo, can be used to screen various compounds or natural products. Such explants can be maintained in minimal culture media for extended periods of time (e.g., for 21 days or longer) and can be contacted with any compound, e.g., small molecule or natural product, e.g., growth factor, to determine the effect of such compound on one of cellular growth, proliferation or differentiation of progenitor cells in the explant. Detection and quantification of growth, proliferation or differentiation of these cells in response to a given compound provides a means for determining the compound's efficacy at inducing one of the growth, proliferation or differentiation in a given ductal explant. Methods of measuring cell proliferation are well known in the art and most commonly include determining DNA synthesis characteristic of cell replication. There are numerous methods in the art for measuring DNA synthesis, any of which may be used according to the invention. In an embodiment of the invention, DNA synthesis has been determined using a radioactive label ($^3$H-thymidine) or labeled nucleotide analogues (BrdU) for detection by immunofluorescence. The efficacy of the compound can be assessed by generating dose response curves from data obtained using various concentrations of the compound. A control assay can also be performed to provide a baseline for comparison. Identification of the progenitor cell population(s) amplified in response to a given test agent can be carried out according to such phenotyping as described above.

Exemplification

The invention now being generally described, it will be more readily understood by reference to the following examples which are included merely for purposes of illustration of certain aspects and embodiments of the present invention, and are not intended to limit the invention.

Preparation of Ductal Explants

Both neonatal and adult rats and mice were used in these studies. After exsanguination by $C0_2$, the common bile duct (CBD) was identified in situ, removed, and placed into a solution of Dulbecco's Modified Eagles Medium (DMEM). The associated pancreatic acinar and islet issue, as well as attached blood vessels were then removed by dissection with forceps. The CBD, along with its associated branches, the main pancreatic ducts, were then sliced transversely into approximately 300 μm long micro-organ explants such that the original epithelial-mesenchymal microarchitecture, e.g. along the transverse axis, of the original organ is retained.

These segments were then cultured in DMEM with the addition of growth factors, either in the presence or absence of collagen type 1 or matrigel, as a growth substrate.

Growth Factors

Effectiveness of the growth factors in stimulating proliferation was judged by the incorporation of Bromodeoxyuridine (BrdU) into DNA by the responding cells. Antibodies to BrdU were used to visualize and characterize the short term responses (24–48 hr).

The long term response was judged by the ability of these populations of cells to be grown and expanded in cell culture as a result of specific growth factor addition.

Three different growth factors (EGF, TGF-α, and bFGF) were used in the following experiments.

1. Administration of EGF to the CBD Explant

Figure 2:
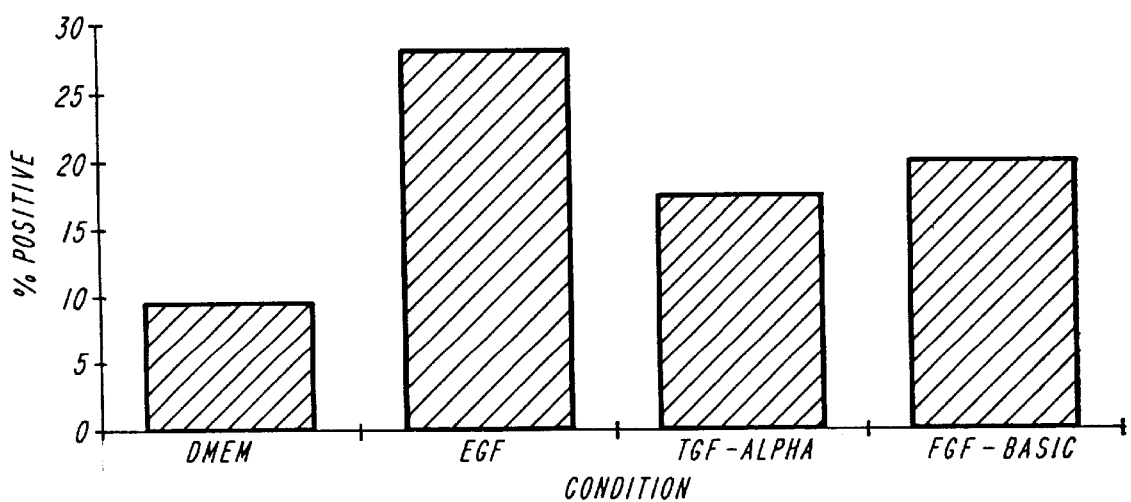
FIG. 2 is a graph depicting the percentage of BrdU labeled positive cells in a common bile duct explant, 24 hours after administration of a growth factor. Growth factors, EGF, TGF-α, and bFGF were administered and DMEM minimal media was used as a control.

EGF was administered in three different doses, 1 ng/ml, 10 ng/ml and 100 ng/ml to the CBD explant. Activation of proliferation as assessed by BrdU labeling occurred with administration of 10 ng/ml of growth factor EGF within a span of 24 hr (FIG. 1 and 2). There was no difference observed between 10 and 100 ng/ml dose. Addition of EGF to the CBD tissue explant resulted in proliferation of distinct cells within the explant and resulted in clustering of these cells.

2. Administration of TGF-α to the CBD Explant

TGF-α was administered in the same doses as EGF. Activation of proliferation as assessed by BrdU labeling occurred with administration of 100 ng/ml of growth factor TGF-α within a span of 24 hr (FIG. 1 and 2). Unlike EGF, administration of TGF-α to the CBD explant resulted in proliferation of cells throughout the explant.

3. Administration of FGFb to the CBD Explant

Figure 3:
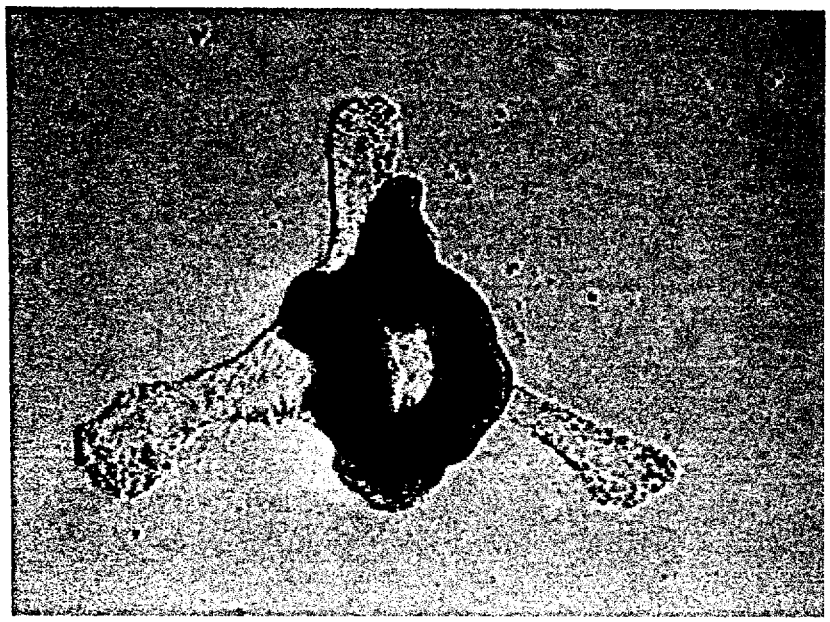
FIG. 3 is a photograph depicting in vitro growth and expansion of the cells within a common bile duct explant in response to administration of growth factor bFGF.

FGFb was administered in the same doses as the above described growth factors. Activation of proliferation as assessed by BrdU labeling occurred with administration of 10 ng/ml of growth factor FGFb within a span of 24 hr (FIG. 1 and 2). Administration of 10 ng/ml of FGFb resulted in induction of distinct CBD structures to synchronously divide, implying organized regulation of proliferative potential and response. FIG. 3 depicts in vitro growth and expansion of CBD explant, e.g., formation of outgrowths, e.g., blebs, in response to administration of FGFb.

Preliminary long term growth experiments indicate that there does exist a large proliferative potential within the CBD explant that can be maintained in culture for at least 21 days.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for isolating progenitor cells from a bile duct comprising culturing a bile duct explant comprising both an epithelial layer and a stromal layer, which explant retains in culture the original epithelial-mesenchymal microarchitecture of a mammalian bile duct, wherein said explant is maintainable in culture for at least twenty-four hours, and wherein said explant includes at least on progenitor cell which has the ability to proliferate;

contacting said explant with an agent which causes proliferation of progenitor cells in said explant; and isolating from said explant progenitor cells that proliferate in response to said agent.

2. The method of claim 1, wherein said agent is a growth factor.

3. The method of claim 2, wherein said growth factor is selected from a group consisting of IGF, EGF, TGF, FGF, HGF, VEGF, and orthologous or paralogous factors thereof.

4. The method of claim 1, wherein said progenitor cells are pancreatic progenitor cells.

5. The method of claim 1, wherein said progenitor cells are hepatic progenitor cells.

6. The method of claim 1, wherein said explant is cultured in medium deficient in biological extracts.

7. The method of claim 1, wherein said medium is deficient in serum.

8. The method of claim 1, wherein said bile duct is a common bile duct.

9. The method of claim 1, wherein said isolated progenitor cells have fewer than 20% of lineage committed cells.

10. The method of claim 1, wherein said explant is from a mammal.

11. The method of claim 10, which mammal is a transgenic mammal.

12. The method of claim 10, which mammal is a primate.

13. The method of claim 12, which mammal is a human.

14. The method of claim 11, which mammal is a miniature swine.

15. The method of claim 4, wherein the progenitor cells express one or more of IPF-1, insulin, amylase, glucagon, and somatostatin.

16. The method of claim 4, wherein the progenitor cells are inducible to differentiate into pancreatic islet cells, e.g., β islet cells, α islet cells, δ islet cells, or φ islet cells.

* * * * *

UNITED STATES PATENT AND TRADEMARK OFFICE
CERTIFICATE OF CORRECTION

PATENT NO. : 5,861,313
DATED : Jan. 19, 1999
INVENTOR(S) : Kevin K. Pang and Monica W. Homa It is certified that error appears in the above-identified patent and that said Letters Patent is hereby corrected as shown below:

Column 20, line 38,

In The Claims:

Claim 14 should read as follows:

--The method of claim 10, which mammal is a miniature swine.--

Signed and Sealed this

Twenty-ninth Day of June, 1999

Attest:

Q. TODD DICKINSON

*Attesting Officer*           *Acting Commissioner of Patents and Trademarks*